United States Patent
Zandifar et al.

(10) Patent No.: US 7,969,475 B2
(45) Date of Patent: Jun. 28, 2011

(54) LOW MEMORY AUTO-FOCUS AND EXPOSURE SYSTEM FOR LARGE MULTI-FRAME IMAGE ACQUISITION

(75) Inventors: Ali Zandifar, Cupertino, CA (US); Anoop K. Bhattacharjya, Campbell, CA (US)

(73) Assignee: Seiko Epson Corporation, Tokyo (JP)

( * ) Notice: Subject to any disclaimer, the term of this patent is extended or adjusted under 35 U.S.C. 154(b) by 319 days.

(21) Appl. No.: 11/778,968

(22) Filed: Jul. 17, 2007

(65) Prior Publication Data

US 2009/0021595 A1    Jan. 22, 2009

(51) Int. Cl.
*H04N 5/228* (2006.01)

(52) U.S. Cl. .......... 348/222.1; 348/218.1; 348/245; 348/362; 382/284; 382/312; 382/318

(58) Field of Classification Search ........ 348/221.1, 348/218.1, 345, 362, 222.1; 382/284, 318, 382/312
See application file for complete search history.

(56) References Cited

U.S. PATENT DOCUMENTS

| | | | |
|---|---|---|---|
| 5,600,350 A | 2/1997 | Cobbs et al. | |
| 5,835,108 A | 11/1998 | Beauchamp et al. | |
| 6,196,652 B1 | 3/2001 | Subirada et al. | |
| 6,485,124 B1 | 11/2002 | King et al. | |
| 6,554,390 B2 | 4/2003 | Arquilevich et al. | |
| 6,686,966 B1 | 2/2004 | Hashimoto | |
| 6,883,892 B2 | 4/2005 | Sievert et al. | |
| 7,030,351 B2 | 4/2006 | Wasserman et al. | |
| 7,777,800 B2 * | 8/2010 | Hoshuyama | 348/345 |
| 2001/0019636 A1 * | 9/2001 | Slatter | 382/284 |
| 2002/0006281 A1 * | 1/2002 | Owada | 396/104 |
| 2003/0117514 A1 * | 6/2003 | Weintroub et al. | 348/345 |
| 2004/0008272 A1 | 1/2004 | Tang | |
| 2004/0169768 A1 * | 9/2004 | Lee et al. | 348/362 |
| 2005/0012847 A1 | 1/2005 | Nakajima et al. | |
| 2006/0215750 A1 | 9/2006 | Izawa | |
| 2006/0257050 A1 * | 11/2006 | Obrador | 382/286 |
| 2009/0021595 A1 * | 1/2009 | Zandifar et al. | 348/222.1 |

FOREIGN PATENT DOCUMENTS

| | | |
|---|---|---|
| JP | 3-183148 | 8/1991 |
| JP | 2000-187165 | 7/2000 |
| JP | 2003-153068 | 5/2003 |

* cited by examiner

*Primary Examiner* — David L Ometz
*Assistant Examiner* — Antoinette T Spinks

(57) ABSTRACT

Embodiments of the invention are described that provide automated and efficient optimization of camera settings. In certain embodiments of the invention, both focus and exposure settings are determined based on an analysis of compressed images taken of a frame. Based on this analysis, the camera focus and exposure settings are set to provide a preferred image quality of the particular frame. This optimization of the focus and exposure settings is performed at each frame within the multi-frame image source. As a result, each frame image is independently optimized and addresses variations, such as light and surface inconsistencies, across the multi-frame image source.

7 Claims, 12 Drawing Sheets

200

LOW MEMORY AUTO-FOCUS AND EXPOSURE SYSTEM FOR LARGE MULTI-FRAME IMAGE ACQUISITION

BACKGROUND

A. Technical Field

The present invention relates generally to camera systems, and more particularly, to efficiently determining focus and exposure settings for a camera system acquiring a photograph of a frame within a multi-frame source image.

B. Background of the Invention

Consistent high-quality image acquisition is oftentimes a challenging task for many camera systems. The resolution requirements of these camera systems may change from application to application. For example, a microscopic resolution of a semiconductor substrate may be required to allow an analysis of the manufactured pattern thereon. Obtaining a full image of the substrate at a microscopic resolution is difficult because of the size of the substrate, the resolution requirements of the image and inclination of the substrate with respect to the camera.

High-resolution cameras are commonly used to generate images of microscopic resolution. The field of view of a high-resolution camera is typically relatively small resulting in the camera being unable to bring the entire substrate within its field of view. In such instances, a high-resolution image of a substrate may be obtained by partitioning the substrate into multiple frames and taking a photograph of each frame. Once all of the frames have been photographed, all of the frame images are combined or stitched together to provide a single image of the substrate. However, maintaining sufficient image quality across each of the frames is frequently difficult to achieve because of variations between each of the frames.

FIG. 1 illustrates an exemplary source image, such as a pattern manufactured on a semiconductor substrate, which is divided into multiple frames or segments. As shown, the source image 110 is divided into equal frames including Segment (1) 120, Segment (2) 130 through Segment (N) 140. Although FIG. 1 shows the frames as having the same shape and area, it may be the case that the source image 110 is divided into unequal frames. Additionally, some or all of the segments may have overlap which all for improvements in the subsequent combination or stitching of the segments into a photograph of the source image 110.

As a camera is moved from one frame to another frame, the quality of the images may degrade. This degradation may result from inconsistent light from one frame to another. In addition, the surface of the pattern or substrate may not be completely smooth resulting in variations in the distance between the pattern surface and the camera. Further yet, the pattern densities and designs may be substantially different from one frame to another which may also affect the quality between the frame images.

The quality of each frame image may be characterized using various different parameters. For example, the quality of a frame may be measured using both contrast and sharpness indicators. One factor that defines the contrast of an image is the exposure setting on the camera. If the exposure setting is not optimized, then the image contrast will likely be over lower quality. One factor that defines the sharpness of the image is the focus setting on the camera. If the focus setting is not optimized, then the image sharpness will appear blurry and the edges within the image will not be defined.

The importance of generating consistently high-quality images is well understood when the images are to be stitched or combined together. If certain frame images are out of focus or have poor contrast, then the stitched image may appear awkward and difficult to analyze. Because a large multi-frame image may require a large number of frame images to be taken, the process of optimizing the camera may be tedious and time consuming.

SUMMARY OF THE INVENTION

Embodiments of the invention are described that provide automated and efficient optimization of camera settings. In certain embodiments of the invention, both focus and exposure settings are determined based on an analysis of compressed images taken of a frame. Based on this analysis, the camera focus and exposure settings are set to provide a preferred image quality of the particular frame. This optimization of the focus and exposure settings is performed at each frame within the multi-frame image source. As a result, each frame image is independently optimized and addresses variations, such as light and surface inconsistencies, across the multi-frame image source.

In various embodiments of the invention, both focus and exposure settings are optimized by analyzing the size of compressed image files generated from photographs taken at different settings of a single frame. For example, a focus setting is identified by taking a plurality of photographs at each of a plurality of focus settings. Each of the plurality of photographs is compressed and an average file size is identified. The photograph generating the largest compressed image file size is identified and the corresponding focus setting is selected. Thereafter, a similar procedure is performed to identify an optimized exposure setting. In both cases, a relationship between the size of a compressed image file and the quality (both sharpness and contrast) of the image is used to efficiently select preferred focus and exposure camera settings. Once the settings are identified for the frame, the camera progresses to the next frame within the multi-frame source image.

These optimization procedures provide not only efficient and relatively quick identification of camera settings, but also allow for low memory demands within the camera system. In certain embodiments of the invention, because the compression of the image may be performed within the camera itself using a hardware implementation, the system does not require significant memory resources within an attached computer or internal memory. This reduction of memory may be further reduced by limiting the amount of compressed images and focus and exposure indicators stored during the analysis procedure. In certain embodiments of the invention, only a single image is saved at a time for purposes of optimization of the auto-focus and/or auto-exposure methods.

One skilled in the art will recognize that various analysis techniques may be used, including the iterative process described above, to select a focus setting and an exposure setting relative to the size of a compressed image file. Furthermore, the progression through the multi-source image file may vary depending on numerous factors known to one of skill in the art.

A camera system is described that provides efficient imaging of a multi-frame image source. The camera system includes a camera, a controller arm, and a processing resource, such as a computer, that is used to calibrate/optimize the camera relative to each frame within the source image. The processing resource may be external to the camera or be integrated within the camera or controller arm. Furthermore, the camera system includes an image compression mechanism that converts photographs into compressed image files. This image compression mechanism may be located anywhere within the system, including the camera itself, and may be realized in hardware, software, or firmware.

Other objects, features and advantages of the invention will be apparent from the drawings, and from the detailed description that follows below.

BRIEF DESCRIPTION OF THE DRAWINGS

Reference will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

Embodiments of the invention are described that provide automated and efficient optimization of camera settings. In certain embodiments of the invention, both focus and exposure settings are determined based on an analysis of compressed images taken of a frame. Based on this analysis, the camera focus and exposure settings are set to provide a preferred image quality of the particular frame. This optimization of the focus and exposure settings is performed at each frame within the multi-frame image source. As a result, each frame image is independently optimized and addresses variations, such as light and surface inconsistencies, across the multi-frame image source.

In the following description, for purpose of explanation, specific details are set forth in order to provide an understanding of the invention. It will be apparent, however, to one skilled in the art that the invention may be practiced without these details. One skilled in the art will recognize that embodiments of the present invention, some of which are described below, may be incorporated into a number of different devices including camera systems, cameras, personal computers and other such devices. The embodiments of the present invention may also be present in software, hardware or firmware. Structures and devices shown below in block diagram are illustrative of exemplary embodiments of the invention and are meant to avoid obscuring the invention. Furthermore, connections between components and/or modules within the figures are not intended to be limited to direct connections. Rather, data between these components and modules may be modified, re-formatted or otherwise changed by intermediary components and modules.

Reference in the specification to "one embodiment" or "an embodiment" means that a particular feature, structure, characteristic, or function described in connection with the embodiment is included in at least one embodiment of the invention. The appearances of the phrase "in one embodiment" in various places in the specification are not necessarily all referring to the same embodiment.

Figure 1:
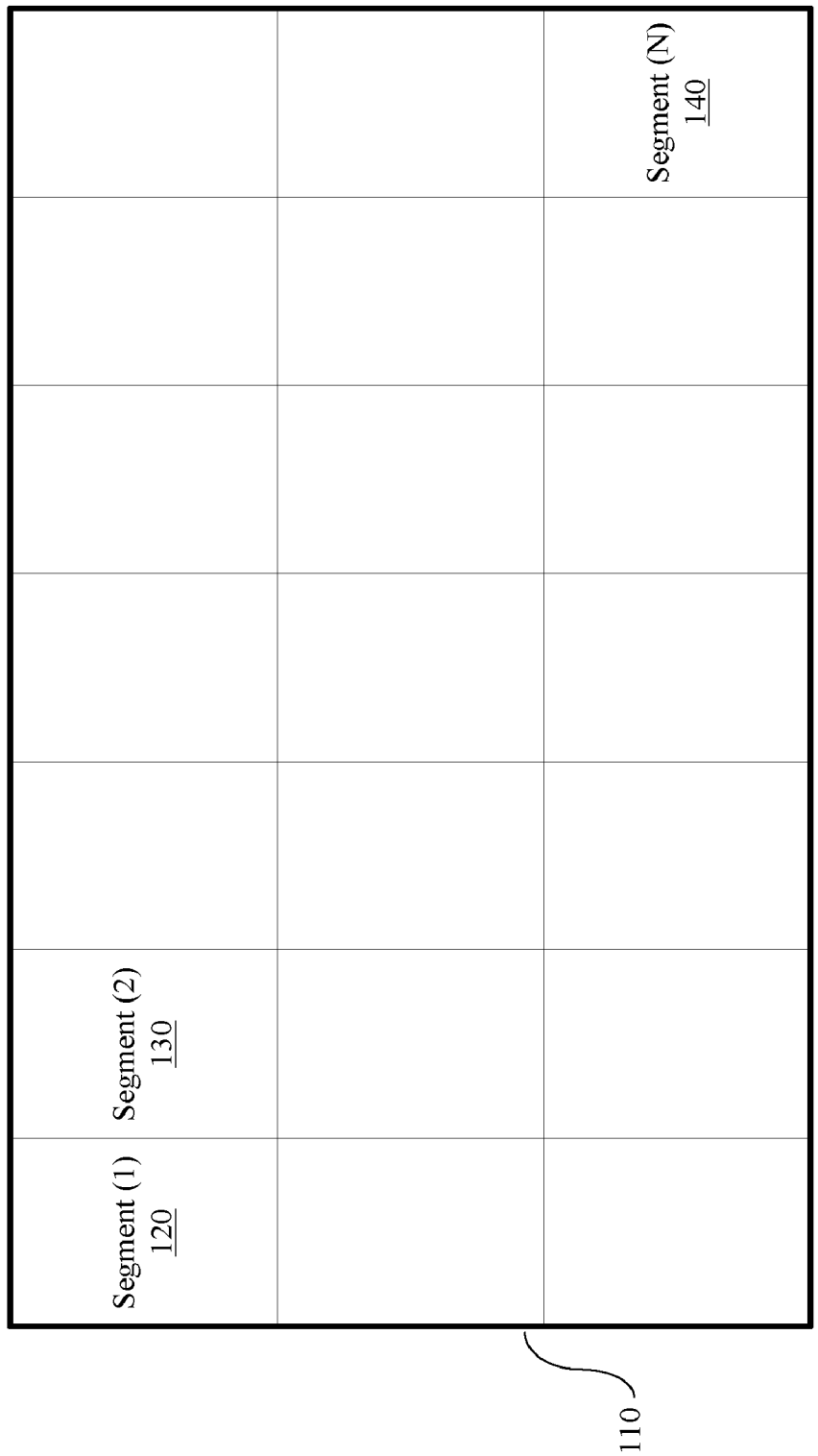
FIG. 1 illustrates a dissection of a source image into multiple image frames to allow higher resolution images to be taken.
Figure 2:
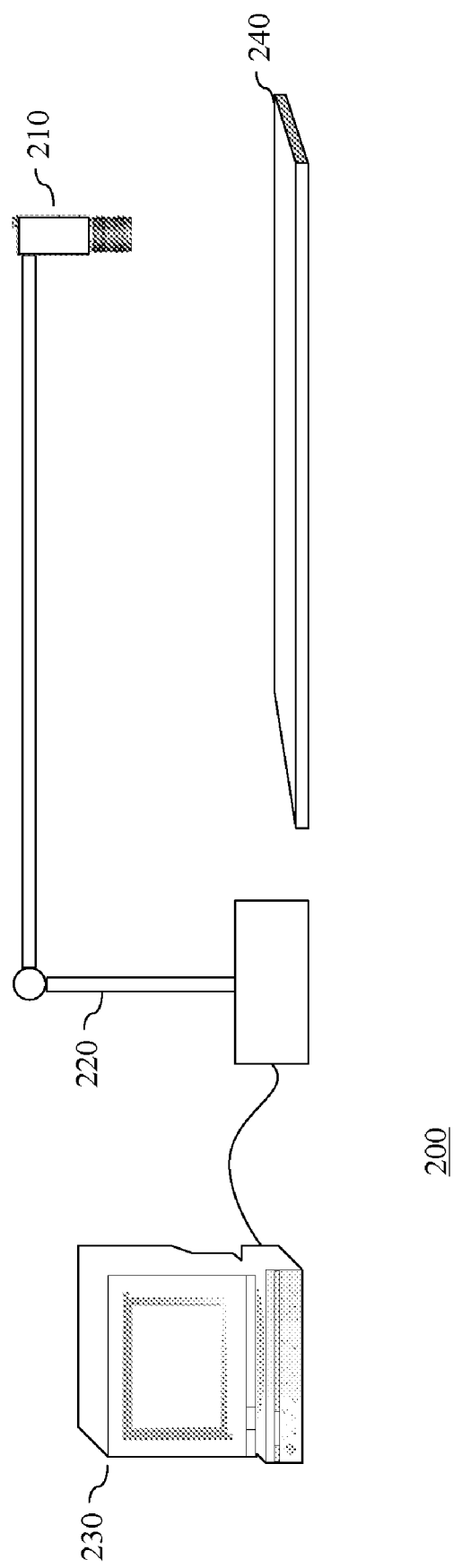
FIG. 2 is a general block diagram of a camera system and multi-frame source image according to various embodiments of the invention.

FIG. 2 illustrates a camera system having automated optimization of focus and exposure settings according to various embodiments of the invention. The camera system 200 includes a camera 210 that is controlled and positioned by a control arm 220. The control arm 220 allows the camera 210 to be positioned within a two-dimensional space above a source image 240. In other embodiments, the control arm 220 may position the camera 210 above the source image 240 in a three-dimensional space. One skilled in the art will recognize that other control structures may be used to control the location of the camera 210 relative to the source image 240 and all of these control structures are intended to fall within the scope of the present invention. Additionally, numerous different types of cameras may be used to capture an image or images of the frames within the source image 240. In certain embodiments, the position of the camera 210 is fixed by the control arm 220 and the source image 240 is movable within a two-dimensional space. For example, the source image 240 may be placed on a backlight table that provide light through the source image 240 and moves the source image so that different segments may be photographed.

The source image 240 may have a light source below (not shown) that illuminates the source image for improvement in quality of the captured image. However, there may be certain instances where there is not a light source specific to the source image 240. In any event, there should be sufficient light to allow the camera 210 to take images of the source image 240.

In various embodiments of the invention, the system 200 also comprises a computer 230 that is connected to the camera. The computer 230 may provide certain processing functions used to optimize both the focus and exposure setting of the camera 210. In other embodiments, the system 200 integrates the processing functions within the camera 210 or the camera control arm 220.

At each frame within the multi-frame source image 240, the camera system 200 is calibrated to improve the quality of the image taken. In various embodiments of the invention, the camera 210 is calibrated at each frame by optimizing a focus setting and an exposure setting. This high-quality image capture adjustment procedure is intended to ensure that the quality of an image taken at each frame meets a preferred image quality threshold. Because this high-quality image capture adjustment occurs independently at each frame, variations between frames are compensated by the camera 210 to provide a more consistent image quality across the entire multi-frame image source 240.

As will be discussed in more detail below, the high-quality image capture adjustment procedure is intended to require minimal resources on the system 210 and provide efficient methods for optimizing both focus and exposure settings. In particular, characteristics of image compression are used to optimize these setting relative to a compressed image file(s) for each frame. In certain embodiments of the invention, the compression operations may be performed in hardware or firmware on the camera 210, which provides a quick and efficient method for compressing the image at a particular frame. In other embodiments, compression is performed at the computer 230 in software, hardware or firmware.

One skilled in the art will recognize that compression of images may be performed in various locations within the camera system 200. Furthermore, the present invention may use numerous different compression techniques that allow quantification of an image quality relative to a characteristic (s) of the compressed image.

The system 200 follows a frame progression along the multiple frames within the source image 240. This progression may vary depending on the system and/or source image that is being captured by the camera 210. FIGS. 3A-3D are representative progression patterns of the camera 210 above the multi-frame source image 240. One skilled in the art will recognize that other progression patterns may be used to capture the source image 240 or portion thereof.

Figure 3A:
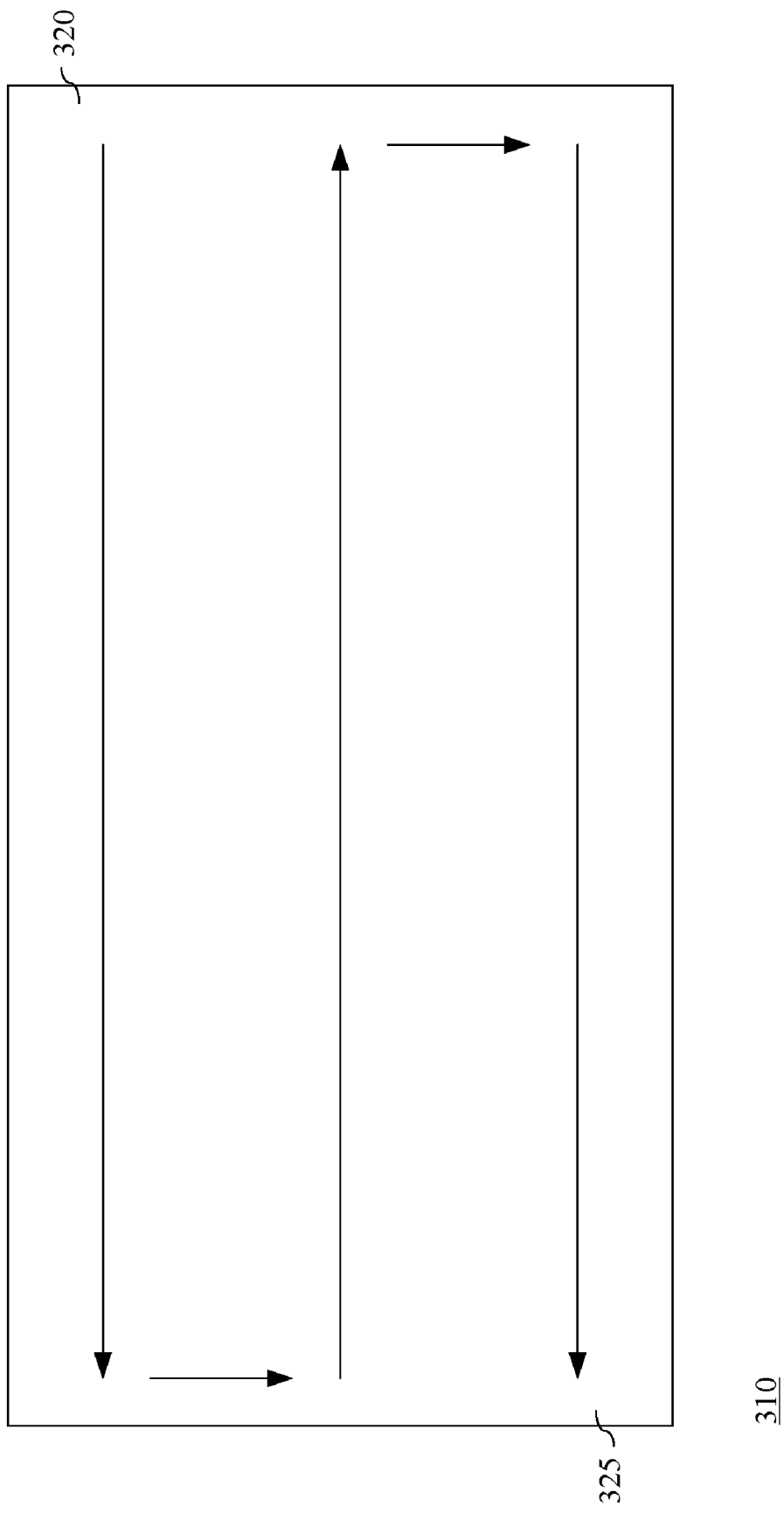
FIG. 3A is an illustration of a multi-frame source image and a sequence order of photographs according to various embodiments of the invention.

FIG. 3A shows a first progression pattern according to various embodiments of the invention. The progression 310 begins at the frame in the upper right corner 320 of a two-dimensional grid above the source image 240. The camera 210 takes an image of each frame in the highest row moving from right to left. Thereafter, the camera 210 moves down a row and progresses from left to right taking a photograph of each of the frames in this second row. In various embodiments, the progression of the camera 210 follows this pattern until the last frame 325 of the source image 240 is reached. In other embodiments of the invention, the camera 210 stops at some frame prior to the final frame 325 of the source image 240 so that only a portion of the image is captured.

Figure 3B:
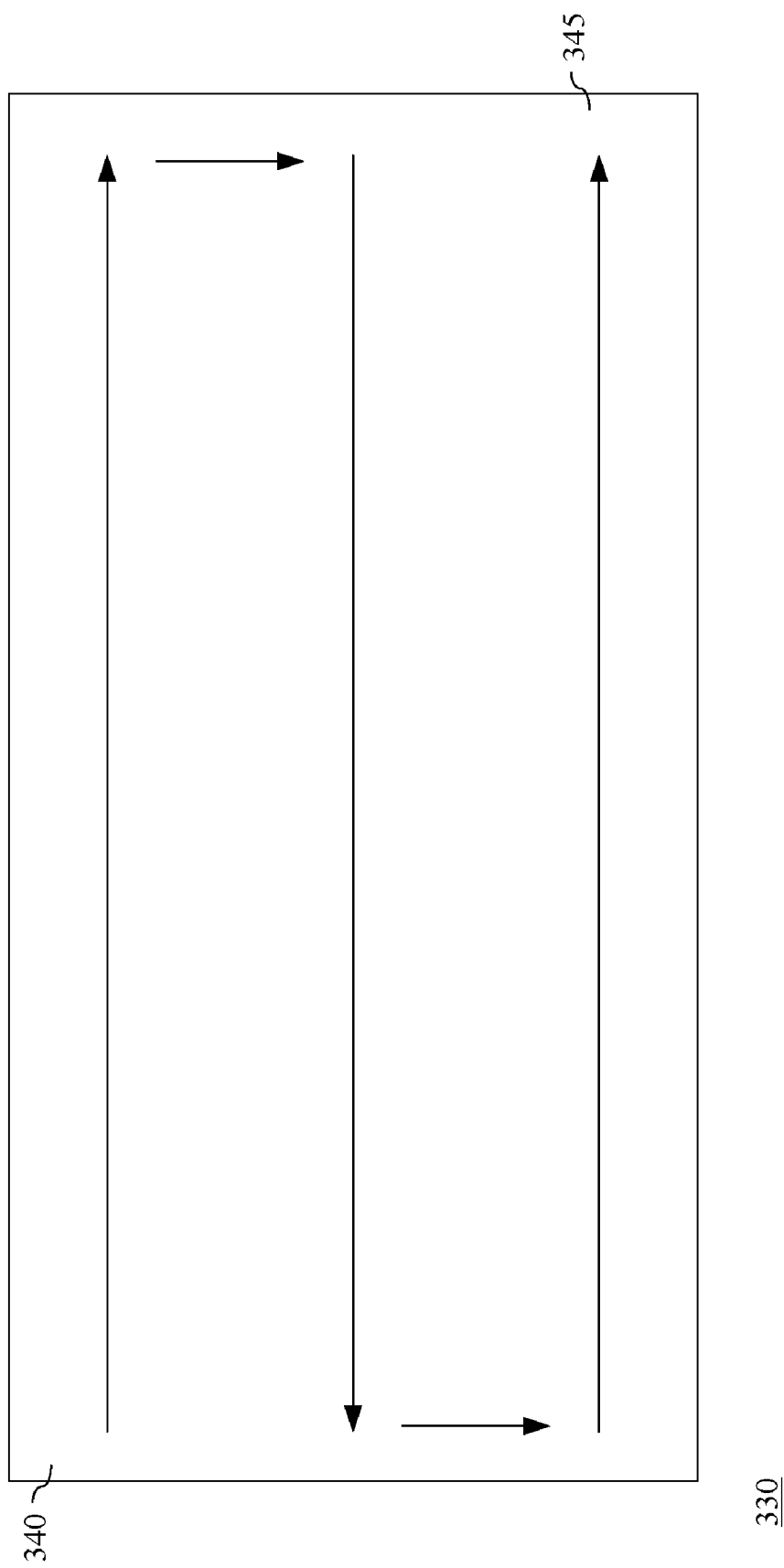
FIG. 3B is another illustration of a multi-frame source image and another sequence order of photographs according to various embodiments of the invention.

FIG. 3B illustrates another progression pattern according to various embodiments of the invention. This progression 330 is similar to the first progression pattern in that frames are imaged row-by-row. In this example, the frame 340 in the upper left corner of the image 240 is used as the starting point. The camera 210 progresses through the source image 240 until it ends at the final frame 345 in the lower right corner. In certain embodiments, the progression need not finish at the final frame 345 but is completed at some frame prior to this final frame 345.

Figure 3C:
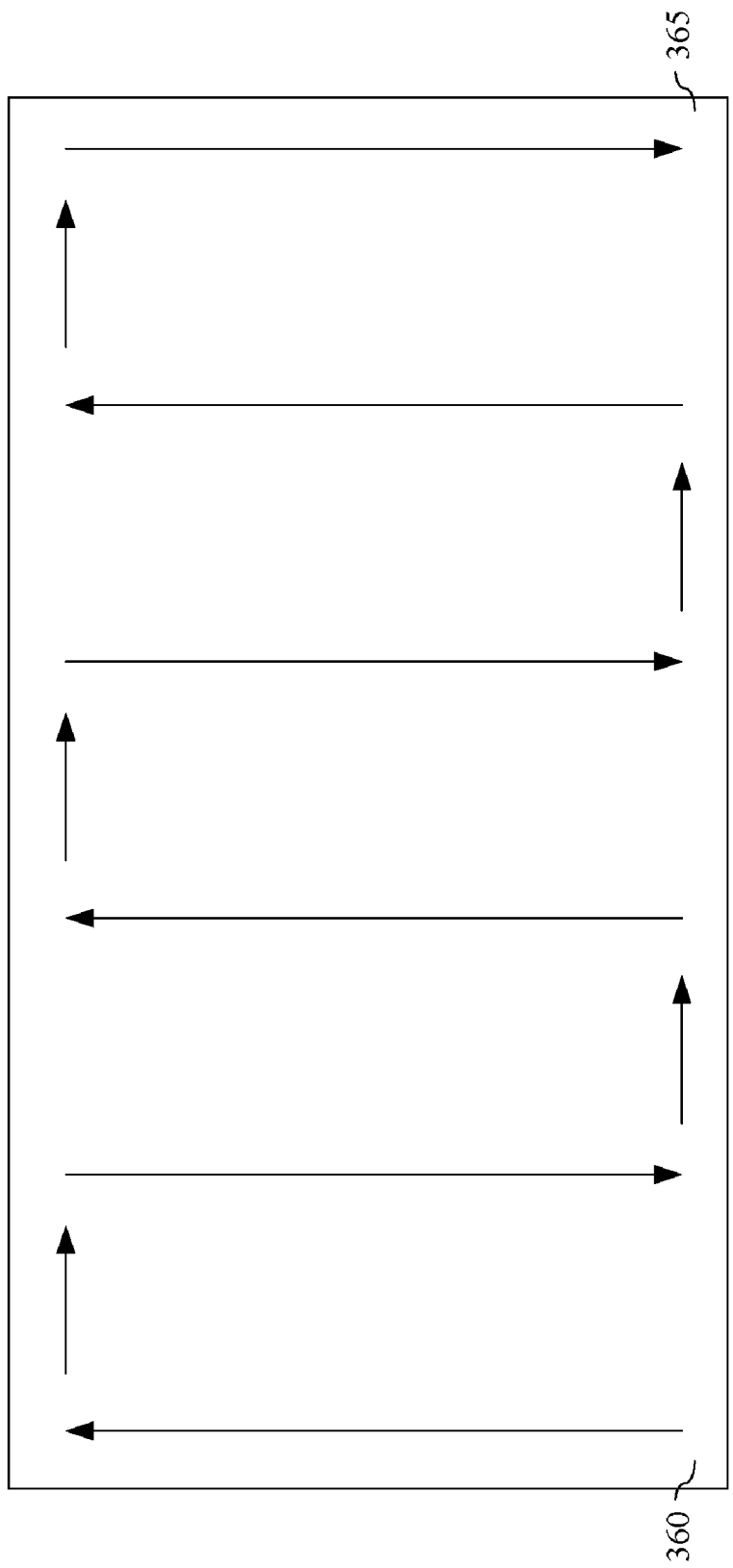
FIG. 3C is yet another illustration of a multi-frame source image and a sequence order of photographs according to various embodiments of the invention.

FIG. 3C illustrates yet another progression pattern according to various embodiments of the invention. The progression 350 proceeds on a column-by-column basis across the multi-source image 240. In this example, the camera 210 is initially positioned above the first frame 360 in the lower left corner. The camera 210 takes a photograph of the first frame 360 and progresses up the first column until reaching the top of the source image 240. The camera 210 then moves to the second column and progresses downward. The camera 210 progresses through this pattern until reaching the final frame 365 in the bottom right corner. Once again, in other embodiments, the camera 210 may stop prior to reaching the final frame 365 so that only a portion of the source image 240 is captured.

Figure 3D:
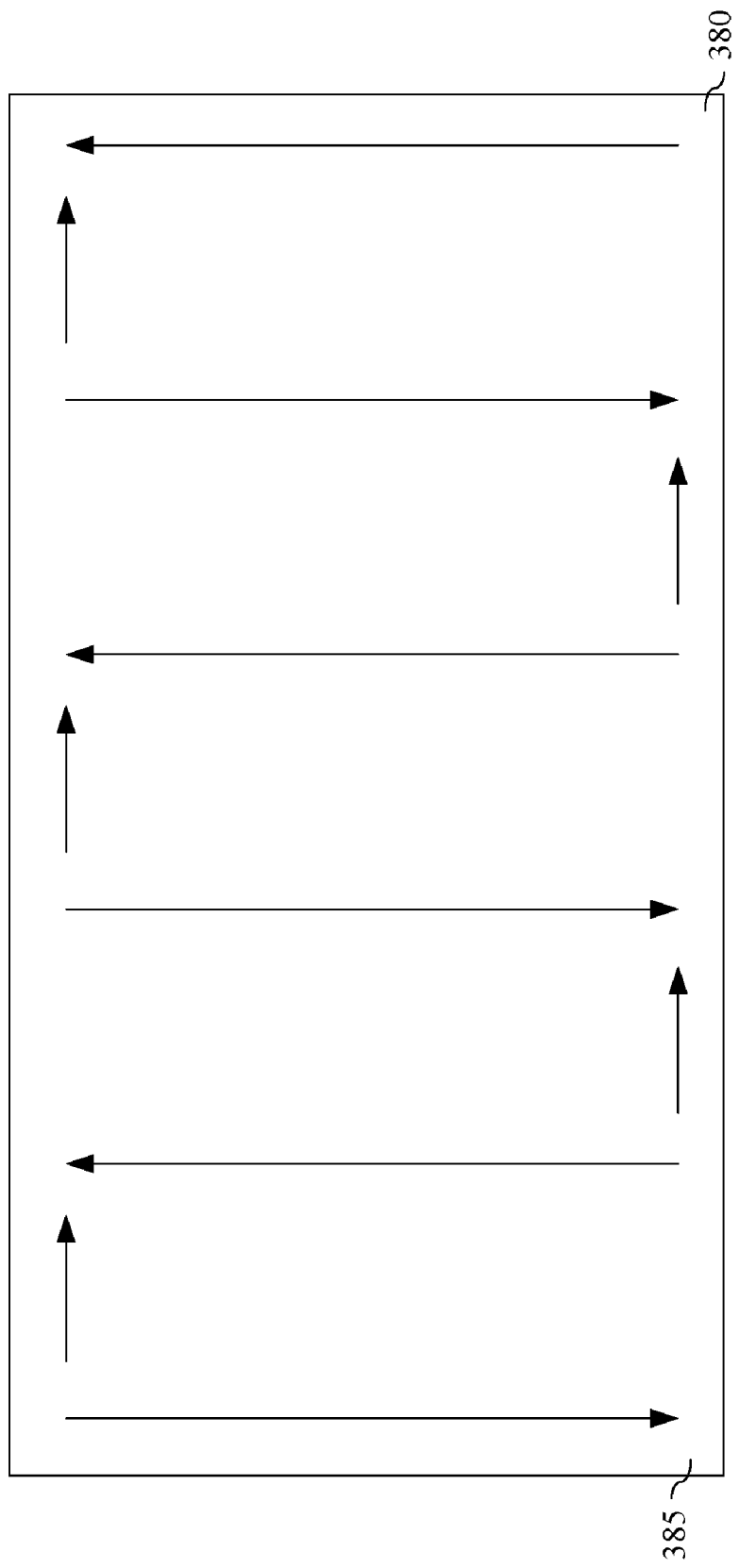
FIG. 3D is an additional illustration of a multi-frame source image and a sequence order of photographs according to various embodiments of the invention.

FIG. 3D illustrates further yet another progression pattern according to various embodiments of the invention. The progression 370 starts at the first frame 380 in the lower right corner and ends at the last frame 385 in the lower left corner. In other embodiments, the camera 210 ends prior to reaching the last frame 385.

One skilled in the art will recognize that numerous different progression patterns may be used to capture the entire source image 240 (frame-by-frame) or a portion of the source image 240 (also frame-by frame). These progressions are not limited to progressing through the image contiguously frame-by-frame, but may use other non-contiguous progression patterns to capture certain frames within the source image 240.

Figure 4:
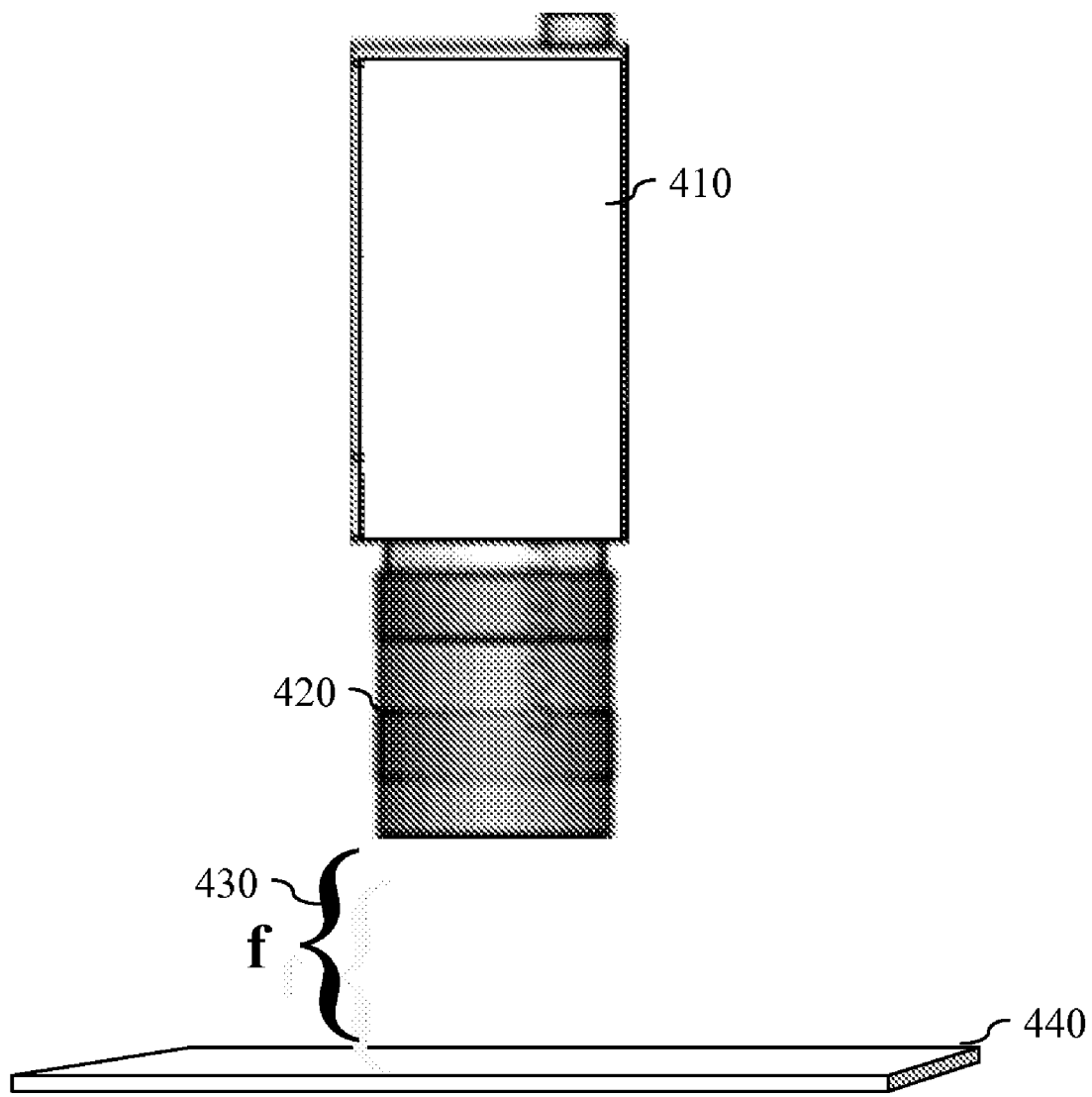
FIG. 4 is an illustration of a camera and frame within a multi-frame image source according to various embodiments of the invention.

As previously mentioned, the camera 210 is optimized at each frame relative to focus and exposure settings. FIG. 4 is intended to show how these settings can affect the image quality of a frame. A camera 410 is located above a frame 440 within the source image 240. A camera lens is located within a housing 420 that allows the lens to be finely adjusted. This adjustment includes moving the lens to change the focal distance (f) 430 between the lens within the camera 410 and the surface of the frame 440.

The camera 410 also includes a shutter that exposes the camera to the surface of the frame 440 for a defined period of time. The length of time or exposure time affects the quality of the image taken of the frame 440. Both the camera focus and the exposure settings are optimized by analyzing a plurality of compressed image files generated by photographs taken of the frame 440. In particular, the focus and exposure settings are optimized by analyzing the resulting size of the compressed image files because high frequency components in the image result in a larger file of the compressed image. These high frequency components are indicative of higher contrast and sharpness of the image taken. Certain methods will be subsequently described in which this relationship between compressed file size and camera settings is utilized to calibrate the camera 410.

Figure 5A:
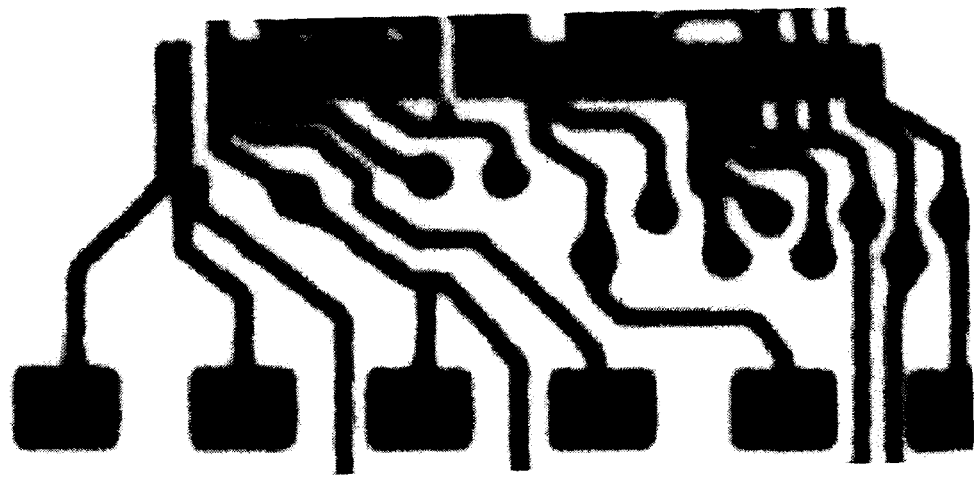
FIG. 5A is an example of an imaged frame using unoptimized focus and/or exposure settings according to various embodiments of the invention.
Figure 5B:
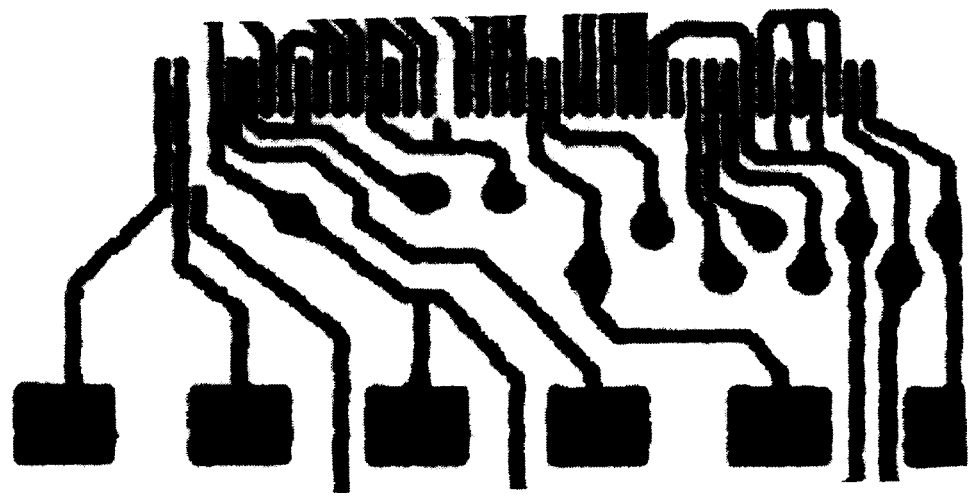
FIG. 5B is an example of an imaged frame using optimized focus and exposure settings according to various embodiments of the invention.

FIGS. 5A and 5B provide a comparative illustration between an optimized source image and an unoptimized source image according to various embodiments of the invention. FIG. 5A shows a representative pattern on a semiconductor substrate having poor contrast and sharpness. In particular, the edges within the pattern are blurred and don't provide sharp edges between foreground and background within the image.

Comparatively, FIG. 5B shows a representative pattern having improved sharpness and contrast according to various embodiments of the invention. The pattern contains much more sharp edges that provide distinction between foreground and background in the image. As in this case, if the source image is an etch pattern, then it is important that the image provide sufficient quality so that an analysis of the traces and components thereon may be properly performed. The camera system may be used to provide just a portion of the pattern in FIG. 5B. Additionally, the camera in the camera system may be adjusted to provide an image at various different granularities. For example, if an engineer would like to perform a detailed analysis of a particular trace or component within the pattern, the camera system may be configured to capture microscopic images of certain frames related to the particular trace or component in the pattern.

Figure 6A:
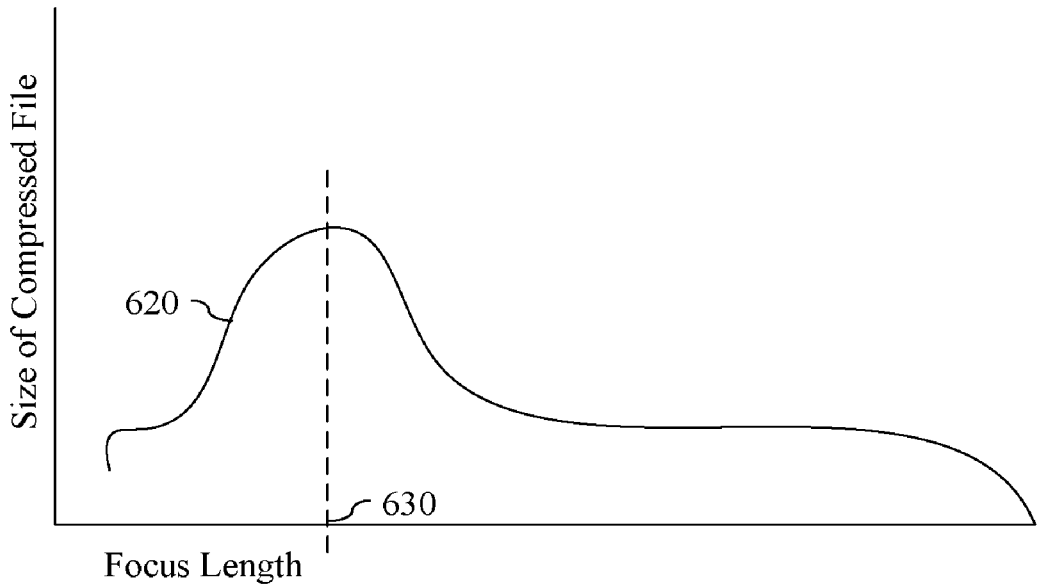
FIG. 6A is a representative plot illustrating a relationship between the size of a compressed file and the focus setting of a camera according to various embodiments of the invention.

FIG. 6A is an illustrative plot, not derived from empirical data, showing a relationship between focus settings of a camera and the size of compressed image files. As previously mentioned, the size of the compressed image file is directly related to the sharpness quality of the image. This relationship may be used to select and/or optimize a focus setting for the camera. In so doing, a plurality of photographs are taken of a particular frame and each of these photographs is compressed. An analysis is performed in which the largest or one of the largest compressed file is identified and the focus setting is selected that was used to take the image that generated this compressed image file. This identified compressed file contains a relatively large amount of high frequency components that are indicative of a high-quality, sharp image.

Referring to the plot 610, a curve 620 is shown that is used to calibrate the focus setting of the camera. On this curve 620, there is a location or locations at which the sharpness quality meets a particular standard. In one example, the focus setting 630 corresponding to the apex of the curve is selected. In another example, a horizontal threshold (not shown) is applied to the curve and one of multiple focus settings above the threshold is selected. In this manner, a sharpness threshold requirement is met for the captured image. One skilled in the art will recognize that numerous methods may be applied, including an iterative process described later, to identify one or more preferred focus settings on the curve 620.

Figure 6B:
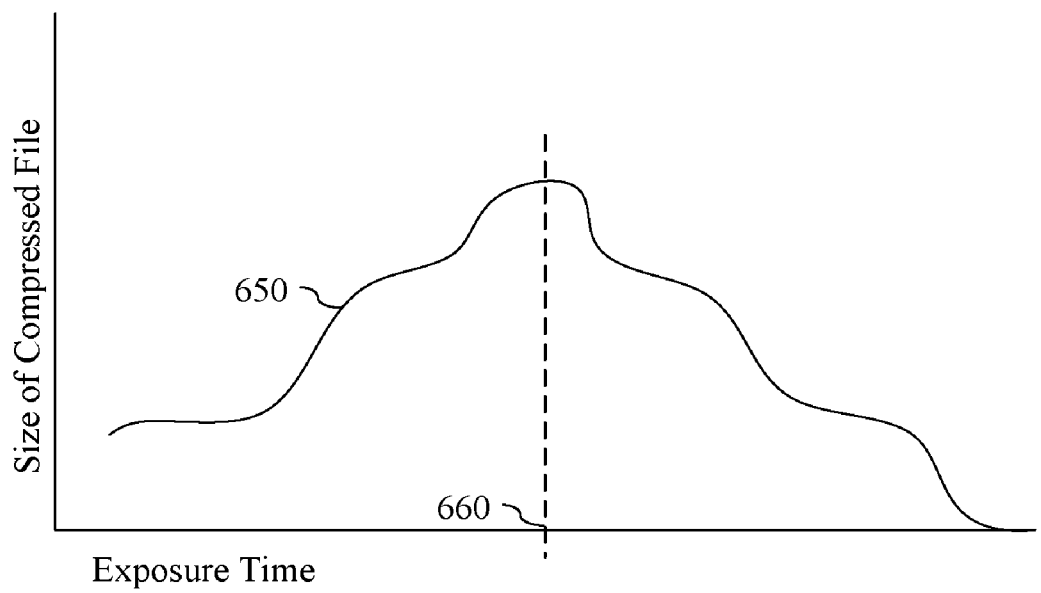
FIG. 6B is a representative plot illustrating a relationship between the size of a compressed file and the exposure setting of a camera according to various embodiments of the invention.

FIG. 6B is an illustrative plot, not derived from empirical data, showing a relationship between exposure settings and the size of compressed image files. The size of the compressed image file is also directly related to the contrast quality of the image. This relationship may also be used to select and/or optimize an exposure setting for the camera. Once again, a plurality of photographs, using the selected focus setting, are taken of the particular frame and each of these photographs is compressed. An analysis is performed in which the largest or one of the largest compressed file is identified and the corresponding exposure setting is selected that was used to take the image that generated this compressed image file.

Referring to the plot 640, a curve 650 is shown that is used to calibrate the exposure setting of the camera. On this curve 640, there is a location or locations at which the contrast quality meets a particular standard. In one example, the exposure setting 630 corresponding to the apex of the curve is selected. In another example, a horizontal threshold (not shown) is applied to the curve and one of multiple exposure settings above the threshold is selected. In this manner, a contrast threshold requirement is met for the captured image. Once again, one skilled in the art will recognize that numerous methods may be applied, including an iterative process described later, to identify one or more preferred exposure settings on the curve 620.

Figure 7:
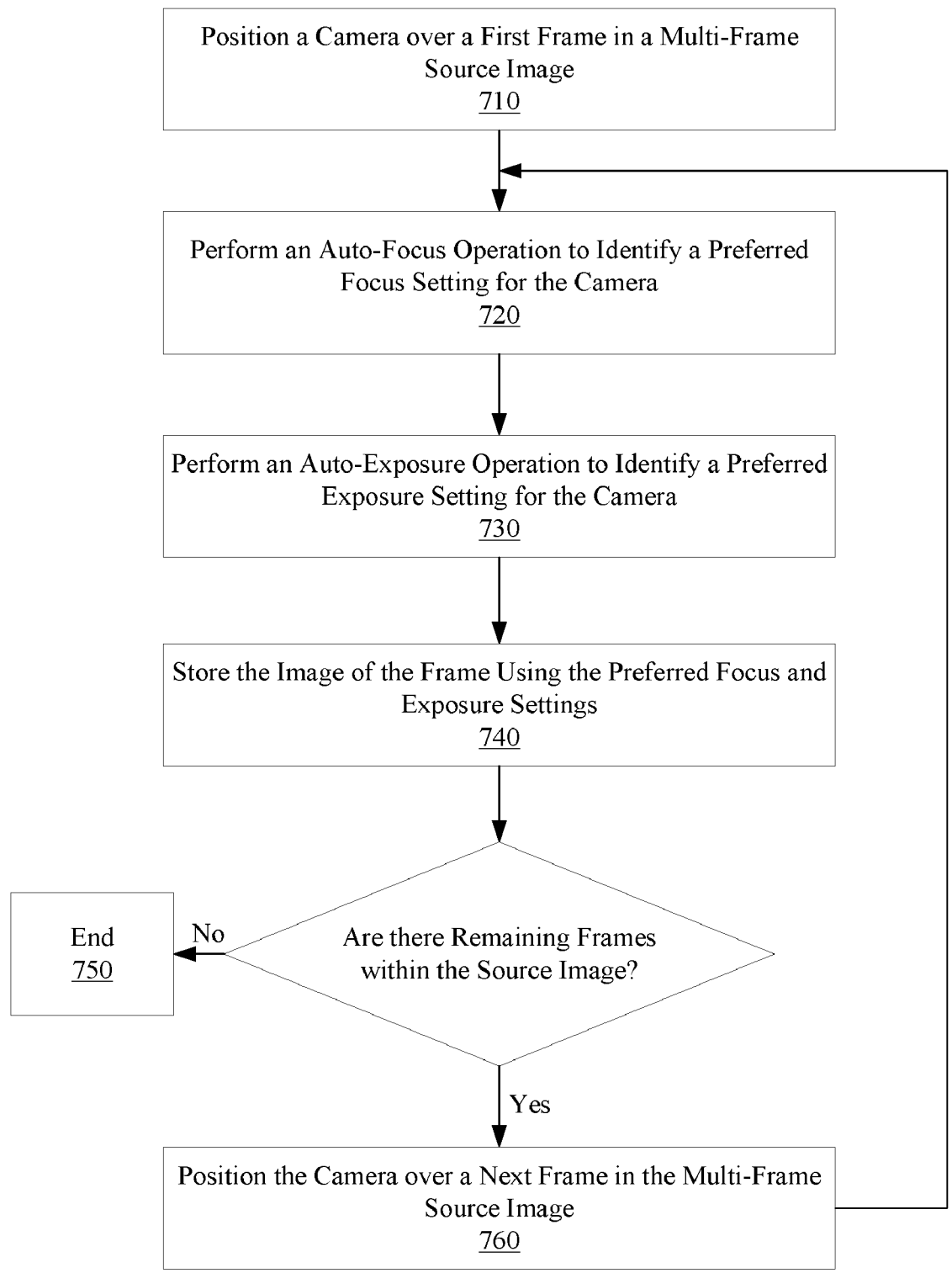
FIG. 7 is a flowchart illustrating a method for optimizing a camera for imaging a multi-frame source image according to various embodiments of the invention.

FIG. 7 is a flowchart illustrating a method for selecting a focus setting and an exposure setting of a camera relative to a frame within a multi-frame source image according to various embodiments of the invention. A camera is positioned over a first frame in the multi-frame source image 710. This first frame may be any frame within the multi-frame source image. An auto-focus operation is performed 720 to identify a preferred focus setting for the camera. According to various embodiments of the invention, this auto-focus operation uses the relationship between image sharpness and the size of the compressed image file to identify this preferred focus setting.

An auto-exposure operation is performed 730 to identify a preferred exposure setting for the camera relative to the first frame. According to various embodiments of the invention, this auto-exposure operation uses a relationship between image contrast and the size of the compressed image file to identify the preferred exposure setting. Once the preferred focus and exposure settings are identified, the corresponding captured image of the first frame is stored 740. A determination is then made as to whether there are additional frames within the multi-frame source image that need to be photographed. If there are no additional frames, then the method is complete 750.

If there are additional frames, then the camera is positioned 760 over the next frame in the multi-frame source image and the auto-focus and auto-exposure operations are performed relative to the next frame. This next frame is oftentimes contiguous to the previous frame; however, there may be instances in which the next frame is a non-contiguous frame.

For purposes of clarity, certain examples are provided below that describe analysis methods for identifying the focus and exposure settings relative to the size of a compressed image file. It is important to note that these examples, in which iteration is used, are not intended to be limiting and there exist various other methods in which these settings may be identified.

Figure 8:
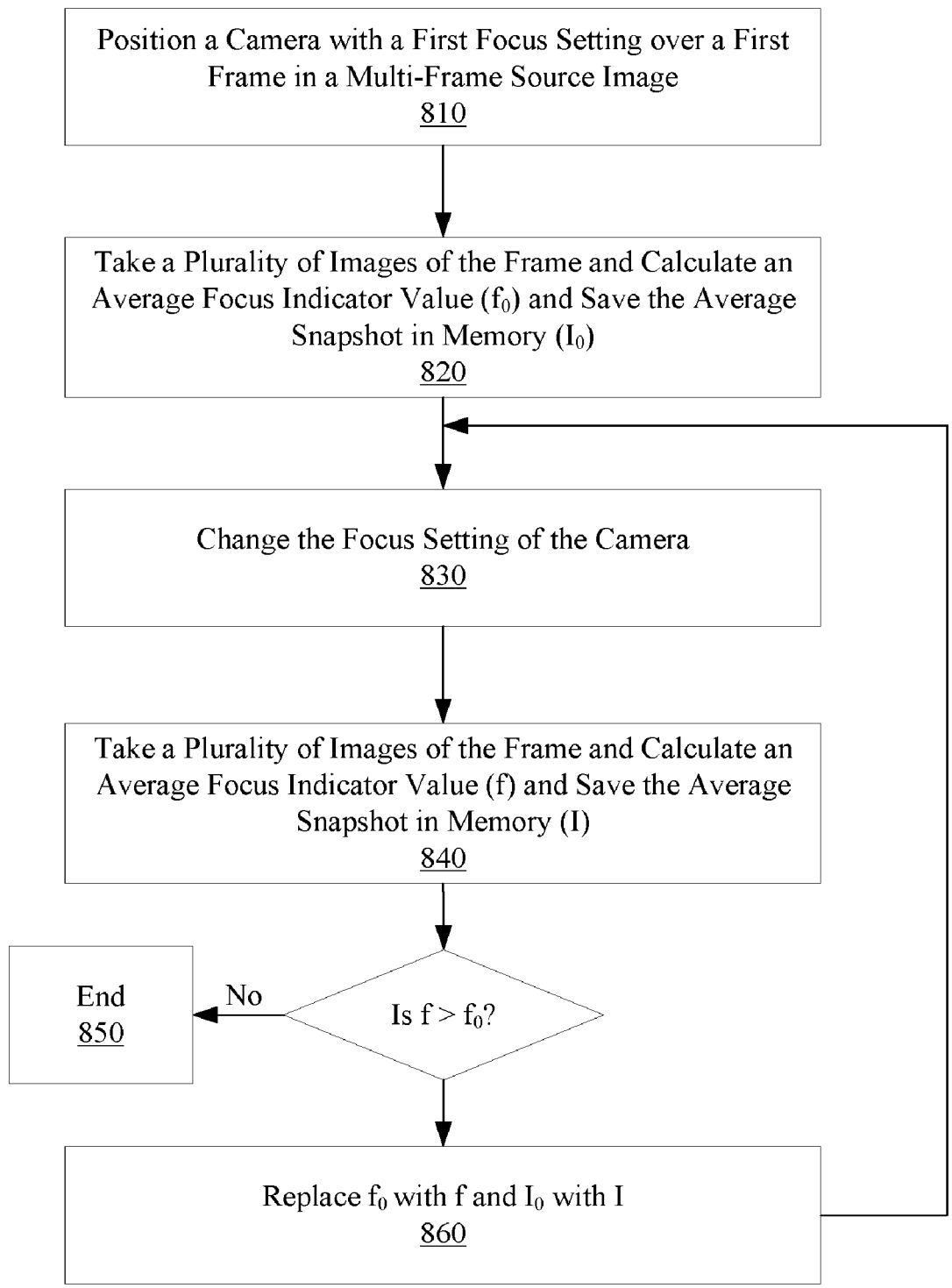
FIG. 8 is a flowchart illustrating a method for determining a preferred focus setting of a camera according to various embodiments of the invention.

FIG. 8 illustrates a method for identifying a focus setting of a camera relative to a frame within an image source according to various embodiments of the invention. A camera is positioned 810 with a first focus setting over a first frame in the multi-frame source image. As previously mentioned, this first frame may be any frame within the source image. Multiple images are taken of the first frame by the camera. An average focus indicator value ($f_0$) is calculated 820 using the plurality of images. In various embodiments of the invention, this average focus indicator value is calculated by computing the average size of compressed image files across the multiple photographs of a segment at the same location. As previously mentioned, certain parameters such as variations in light may affect the quality of the image. By taking multiple photographs of the first frame, compressing these photographs, and averaging the size of the compressed files, a more predictable representation of the photograph using the first focus setting is obtained. Various types of compression techniques may be used including, but not limited to, JPEG and TIFF file formats and variations thereof. This average focus indicator is saved in memory located within the system. The average photograph ($I_0$) corresponding to the average focus indicator is also saved in memory.

The focus setting of the camera is changed 830 to test its image sharpness relative to the previous setting. Using this new setting, multiple images of the frame are taken and compressed. Another average focus indicator (f) is calculated 840 and the corresponding average photograph (I) is identified. This other average focus indicator (f) and its corresponding average photograph (I) are saved within memory.

A comparison of the first average focus indicator ($f_0$) and the other average focus indicator (f) is performed to identify which focus setting generated the larger average compressed image file. In various embodiments of the invention, this comparison effectively identifies the image with the larger amount of high frequency components, which is indicative of sharp edges within the image.

If the first average focus indicator ($f_0$) is larger than the other average focus indicator (f), then the procedure is complete 850 and the focus setting corresponding to the first average focus indicator ($f_0$) is selected. However, if the first average focus indicator ($f_0$) is smaller than the other average focus indicator (f), then the value in the first average focus indicator is replaced 860 with the value in the other average focus indicator (f). Additionally, first average photograph ($I_O$) is replaced by the other average photograph (I).

Thereafter, the focus setting on the camera is once again adjusted and the iterative comparison occurs once again. This procedure allows for iterative progression along the curve 620 to try and identify a value at the apex or near to it. One skilled in the art will recognize that a more complex iterative process may be performed in which slight dips in the curve 620 are compensated by averaging multiple previously calculated average focus indicators.

Figure 9:
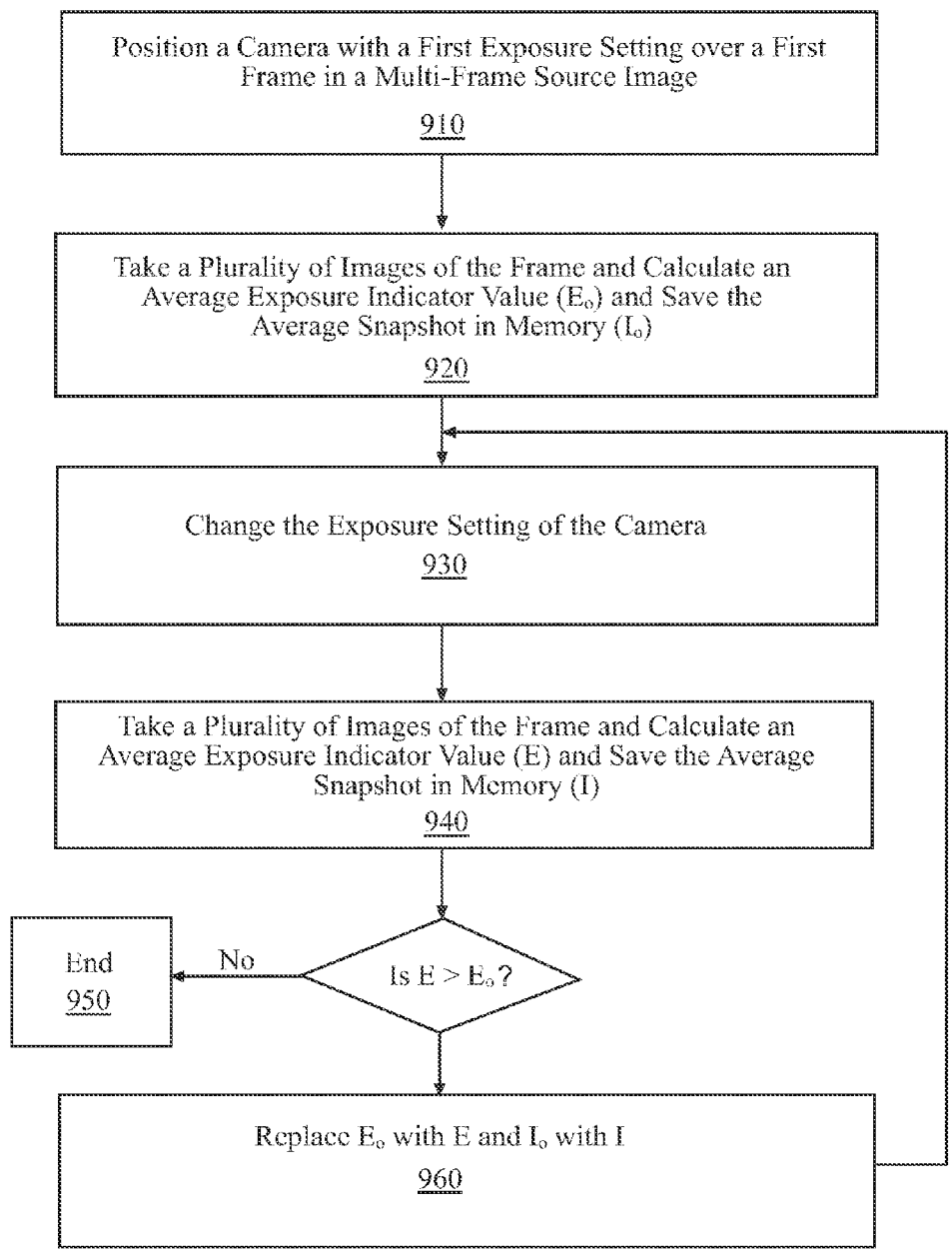
FIG. 9 is a flowchart illustrating a method for determining a preferred exposure setting for a camera according to various embodiments of the invention.

FIG. 9 illustrates a method for identifying an exposure setting of a camera relative to a frame within an image source according to various embodiments of the invention. A camera is positioned 910 over a first frame using the previously identified optimal focus setting and with a first exposure setting over a first frame. Multiple images are taken of the first frame by the camera. An average exposure indicator value ($E_O$) is calculated 920 using the plurality of images. In various embodiments of the invention, this average exposure indicator value is calculated by computing the average size of compressed image files across the multiple photographs. By taking multiple photographs of the first frame, compressing these photographs, and averaging the size of the compressed files, a more predictable representation of the photograph using the first exposure setting is obtained. Once again, various types of compression techniques may be used including, but not limited to, JPEG and TIFF file formats and variations thereof. This average exposure indicator is saved in memory located within the system. The average photograph ($I_O$) corresponding to the average exposure indicator is also saved in memory.

The exposure setting of the camera is changed 930 to test its image contrast relative to the previous setting. Using this new setting, multiple images of the frame are taken and compressed. Another average exposure indicator (E) is calculated 940 and the corresponding average photograph (I) is identified. This other average exposure indicator (E) and its corresponding average photograph (I) are saved within memory.

A comparison of the first average exposure indicator ($E_O$) and the other average exposure indicator (E) is performed to identify which exposure setting generated the larger average compressed image file. In various embodiments of the invention, this comparison effectively identifies the image with the larger amount of high frequency components, which is indicative of high-quality contrast within the image.

If the first average exposure indicator ($E_O$) is larger than the other average focus indicator (E), then the procedure is complete 950 and the exposure setting corresponding to the first average exposure indicator ($E_O$) is selected. However, if the first average exposure indicator ($E_O$) is smaller than the other average exposure indicator (E), then the value in the first average exposure indicator ($E_O$) is replaced 960 with the value in the other average exposure indicator (E). Additionally, the first average photograph ($E_O$) is replaced by the other average photograph (E).

Thereafter, the exposure setting on the camera is once again adjusted and the iterative comparison occurs once again. Similar to the method shown in FIG. 8, this procedure allows for the iterative progression along the curve 650 to try and identify a value at the apex or near to it. Once again, one skilled in the art will recognize that a more complex iterative process may be performed in which slight dips in the curve 650 are compensated by averaging multiple previously calculated average exposure indicators.

While the present invention has been described with reference to certain exemplary embodiments, those skilled in the art will recognize that various modifications may be provided. Accordingly, the scope of the invention is to be limited only by the following claims.

We claim:

1. A system for capturing and processing multiple images of each of multiple frames of an image source, the system comprising:
   a camera, having an adjustable exposure setting and an adjustable focus setting, configured to capture a plurality of images of each frame;
   a control structure, coupled to the camera, that moves the camera within a three-dimensional space above the multi-frame image source to move the camera from one frame to another frame to capture different segments of the image source;
   an image compression mechanism configured to receive the images captured by the camera and to compress the images into compressed images;
   a memory configured to store the compressed images; and
   a processor, coupled to the memory, that identifies a preferred exposure setting and a preferred focus setting for each frame, independently of the other frames, by examining a first set of compressed images of that frame captured at a first focus setting, calculating a first average file size of the first set of compressed images, examining a second set of compressed images of that frame captured at a second focus setting, calculating a second average file size of the second set of compressed images, and comparing the first average file size to the second average file size to identify the preferred focus setting based on which focus setting generated the larger average compressed image file, the processor being further configured to combine the multiple frames, each captured at its independently determined preferred exposure and focus settings, together to form a single image.

2. The system of claim 1, wherein the image compression mechanism is located within the camera as a hardware device.

3. A system for capturing and processing multiple images of each of multiple frames of an image source, the system comprising:
   a camera, having an adjustable exposure setting and an adjustable focus setting, configured to capture a plurality of images of each frame;
   a control structure, coupled to the camera, that moves the camera within a three-dimensional space above the multi-frame image source to move the camera from one frame to another frame to capture different segments of the image source;
   an image compression mechanism configured to receive the images captured by the camera and to compress the images into compressed images;
   a memory configured to store the compressed images; and
   a processor, coupled to the memory, that identifies a preferred exposure setting and a preferred focus setting for each frame, independently of the other frames, by examining a first set of compressed images of that frame captured at a first exposure setting calculating a first average file size of the first set of compressed images, examining a second set of compressed images of that frame captured at a second exposure setting, calculating a second average file size of the second set of compressed images, and comparing the first average file size value to the second average file size to identify the preferred exposure setting based on which exposure setting generated the larger average compressed image file, the processor being further configured to combine the multiple frames, each captured at its independently determined preferred exposure and focus settings, together to form a single image.

4. A method for calibrating a camera for acquisition of a first frame within a multi-frame source image, the method comprising:
    taking a first plurality of photographs of the first frame using a first focus setting on the camera;
    compressing the first plurality of photographs into a first plurality of compressed image files;
    calculating a first average size of the first plurality of compressed image files;
    taking a second plurality of photographs of the first frame using a second focus setting on the camera;
    compressing the second plurality of photographs into a second plurality of compressed image files;
    calculating a second average size of the second plurality of compressed image files; and
    selecting a preferred focus setting on the camera by comparing the first average size to the second average size to identify the focus setting that generated the larger average compressed image file;
    wherein the steps are repeated for each frame of the multi-frame source image to determine a preferred camera focus setting for each frame independently of the other frames; and
    combining the multiple frames, each captured at its independently determined preferred setting, to form a single image.

5. The method of claim 4, further comprising the steps of:
    taking a third plurality of photographs of the first frame using a third focus setting on the camera;
    compressing the third plurality of photographs into a third plurality of compressed image files;
    calculating a third average size of the third plurality of compressed image files; and
    updating the preferred focus setting on the camera for the given frame by comparing the third average size to an average compressed image file size corresponding to the previous preferred focus setting to identify the focus setting that generated the larger average compressed image file.

6. A method for calibrating a camera for acquisition of a given frame within a multi-frame source image, the method comprising the steps of:
    taking a first plurality of photographs of the given frame using a first exposure setting on the camera;
    compressing the first plurality of photographs into a first plurality of compressed image files;
    calculating a first average size of the first plurality of compressed image files;
    taking a second plurality of photographs of the given frame using a second exposure setting on the camera;
    compressing the second plurality of photographs into a second plurality of compressed image files;
    calculating a second average size of the second plurality of compressed image files;
    selecting a preferred exposure setting on the camera for the given frame by comparing the first average size to the second average size to identify the exposure setting that generated the larger average compressed image file;
    wherein the steps are repeated for each frame of the multi-frame source image to determine a preferred camera exposure setting for each frame independently of the other frames; and
    combining the multiple frames, each captured at its independently determined preferred setting to form a single image.

7. The method of claim 6, further comprising the steps of:
    taking a third plurality of photographs of the given frame using a third exposure setting on the camera;
    compressing the third plurality of photographs into a third plurality of compressed image files;
    calculating a third average size of the third plurality of compressed image files; and
    updating the preferred exposure setting on the camera for the given frame by comparing the third average size to an average compressed image file size corresponding to the previous preferred exposure setting to identify the exposure setting that generated the larger average compressed image file.

* * * * *